(12) United States Patent
Thompson

(10) Patent No.: US 6,577,901 B2
(45) Date of Patent: Jun. 10, 2003

(54) NETWORK COMPATIBLE RF WIRELESS LINK FOR MEDICAL DEVICE DATA MANAGEMENT

(75) Inventor: David L. Thompson, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/887,223

(22) Filed: Jun. 22, 2001

(65) Prior Publication Data

US 2002/0013614 A1 Jan. 31, 2002

Related U.S. Application Data (60) Provisional application No. 60/213,330, filed on Jun. 22, 2000.

(51) Int. Cl.$^7$ .................................................. A61N 1/08
(52) U.S. Cl. ........................................................ 607/60
(58) Field of Search ............................... 607/30, 32, 60, 607/16, 9; 600/510

(56) References Cited

U.S. PATENT DOCUMENTS

| | | | |
|---|---|---|---|
| 4,476,868 A | 10/1984 | Thompson | 128/419 PG |
| 5,052,388 A | 10/1991 | Sivula et al. | 128/419 PG |
| 5,113,869 A | 5/1992 | Nappholz et al. | 128/696 |
| 5,336,245 A | 8/1994 | Adams et al. | 607/32 |
| 5,683,432 A | 11/1997 | Goedeke et al. | 607/32 |
| 5,720,770 A | 2/1998 | Nappholz et al. | 607/30 |
| 5,752,976 A | 5/1998 | Duffin et al. | 607/32 |
| 5,843,139 A | 12/1998 | Goedeke et al. | 607/32 |
| 5,957,861 A | 9/1999 | Combs et al. | 600/547 |

FOREIGN PATENT DOCUMENTS

| | | | |
|---|---|---|---|
| WO | WO 96/11722 | 4/1996 | A61N/1/36 |

OTHER PUBLICATIONS

"Designing Bluetooth Connectivity into Portables" Sep. 1999 pp. 61–63 *Portable Design*.

*Primary Examiner*—Scott M. Getzow
(74) *Attorney, Agent, or Firm*—Girma Wolde-Michael (57) ABSTRACT

A network compatible RF Wireless Link for Medical Device Data Management includes apparatus for establishing a communication link between an IMD, a patient-worn device, and a remote monitoring station while at the same time minimizing device current drain. The minimal current drain is achieved by scheduling periodic interrogation of the data collected by the IMDs for subsequent transmission to a remote location. Generally, the communication system is implemented to transmit data preferably telemetered from the IMD to a patient-worn device. The data from the patient-worn device is transmitted to a transceiver that sends the data to a remote information network. The patient-worn device may be equipped with a Bluetooth (BT) or Home RF communication system. The transceiver is preferably similarly equipped with BT or Home RF technology having a plurality of nodes. In one aspect of the invention, the patient-worn device would transmit data to the transceiver, which may be connected to a phone line, cellular phone, satellite communication systems, telemetry or equivalent wireless data transmission system. The system provides patient mobility while enabling data transmission and interrogation of one or more implanted medical devices in the patient.

4 Claims, 6 Drawing Sheets

NETWORK COMPATIBLE RF WIRELESS LINK FOR MEDICAL DEVICE DATA MANAGEMENT

RELATED APPLICATIONS

This application claims priority to provisionally-filed patent application having Ser. No. 60/213,330 filed Jun. 22, 2000, and which is incorporated herein by reference in its entirety.

FIELD OF THE INVENTION

The present invention relates to the field of implanted medical devices (IMDs) and related data management. Specifically, the invention relates to network compatible RF wireless link or equivalent, configured to enable connectivity between various devices.

BACKGROUND OF THE INVENTION

During the latter portion of the twentieth century, it became common to implant IMDs to provide therapy for a vast number of medical conditions. Such devices included electrical stimulation devices, pain control devices, and drug delivery systems. Additionally and as these devices became more complex, it became necessary to monitor both their operation and the patient's condition.

At the same time, patients with IMDs have come to expect a fuller life post implant. These expectations include few, if any, restrictions on their lifestyle. Thus, it has become imperative that patients be allowed a great degree of mobility while their medical condition is being monitored and/or treated by the IMD. The traditional method of semi-annual or annual checkups for the IMD and the patient limits the frequency of monitoring. Moreover, the patient may feel that he must remain close to the physician's clinic or the hospital where checkups take place. Further, emergency situations may sometimes occur which, in the mind of the elderly patient, demand very close proximity to the attending physician.

Moreover, advances in modern patient therapy and treatment have made it possible to implant a number of devices in a single patient. Successful management of the operation and assessment of the performance of each device in these patients may require monitoring these devices for periodic and frequent updates. Further, communication between the various IMDs in order to gain a complete medical history of the patient may be preferred so as to provide a coordinated clinical therapy. Going to the clinic for frequent checks may impose a considerable burden on the patient as well as an overall increase in the cost of health care. Accordingly, it is vital to have IMDs that are equipped with a communications system that connect to a link in such a manner that is transparent to the patient and yet provides the medical data required by the physician.

New developments in telehealth and telemedicine provide one avenue to address these issues. Telehealth is generally defined as the delivery of health care services from provider to patient via telecommunications links. Telemedicine, on the other hand, involves communications between health care providers and patients. Both of these technologies are intended to reduce the overall cost of medical care, as well as improving the access of patients to health care services. In the context of IMDs, developing systems that allow patients to be monitored remotely in the home require critical modular instrument technology as well as communications systems. This technology can help reduce the number of home visits and provide more time for the health care provider to respond to changes in the patient's condition.

U.S. patent application Ser. No. 09/745,112, filed Dec. 20, 2000, "Instrumentation and Software for Remote Monitoring and Programming of Implantable Medical Devices (IMDs)", incorporated by reference herein in its totality, describes a modular system that is adaptable to a variety of medical devices. The system includes communications technology to effect wireless transmission between various devices, patients, and health care providers.

As can be seen from the patents cited in the '112 application, telemetry has been proposed as one of the communications systems. A system is taught in U.S. Pat. No. 5,113,869 that describes an implanted ambulatory ECG patient monitor with a longer range telemetry communication capability. One of the external devices disclosed in the '869 patent is a wrist-worn alarm that emits an audible warning signal to alert the patient that the implanted ECG monitor has detected an arrhythmia. Another external device in the '869 patent is a belt-worn "full disclosure recorder" containing a high capacity memory for receiving and storing data telemetered from the implanted ECG monitor when its memory capacity is exhausted.

A similar method of communication for an implanted pacemaker-cardioverter-defibrillator device is disclosed in U.S. Pat. No. 5,336,245. The '245 patent teaches how data accumulated in the limited capacity memory of the IMD is transferred to a larger capacity external data recorder. The accumulated data is then forwarded via a modem-equipped computer-based device to a clinic.

RF coupled systems are extensively employed communications systems in modern IMDs. In such systems, information is transferred from a transmitting coil to a receiving coil by way of a radio-frequency carrier signal. The carrier signal is modulated with the data that is transmitted through the use of an appropriate modulation scheme, such as phase shift keying (PSK), frequency shift keying (FSK), or pulse position modulation (PPM), among others. These systems, however, have been used primarily to achieve communications between an IMD and an external programmer. Issues related to this type of communication are disclosed in U.S. Pat. Nos. 5,683,432 and 5,843,139 issued to Goedeke, et al., both incorporated herein by reference in their totality.

Advances in the art have made it possible to monitor IMDs and the patient from just about anywhere in the world. Such a system is disclosed in U.S. Pat. No. 5,752,976 issued to Duffin et al., and incorporated herein by reference in its entirety. This system provides means for communicating with an IMD implanted in a mobile patient. The IMD includes a telemetry transceiver for communicating data to an external device either worn by the patient or located in close proximity to the patient. The communicated data is then transferred to a remote medical support network.

Implementation and operation of most, if not all, RF communication systems involves a balancing or compromising of certain countervailing considerations. These are associated with such interrelated operational parameters as data transmission rate and transmission range, among numerous others. For example, the adjustment of one operating parameter may permit or require the adjustment of one or more other operating parameters. At the same time, predetermined system performance goals and/or requirements must be met. Moreover, predetermined limitations imposed upon operational parameter adjustment must be adhered to. These conditions result in the trade-off between signal range and signal power. Simply stated, for a given communication scheme, a more powerful (e.g., higher amplitude) signal has a longer effective range. Thus, decreasing the range of a communication link (e.g., reducing the distance between transmitters and receivers in the link) allows the transmission power to be decreased, while other operational parameters, e.g., data transmission rate, can be held at a constant value.

Another example is the trade-off between data transmission rate and transmitted signal power. Those skilled in the art will appreciate that, in most instances, increasing the data transmission rate over an RF channel typically requires increased signal bandwidth. Increasing the bandwidth, in turn, tends to lead to increased power consumption by the communication system in order to maintain an acceptable signal-to-noise ratio.

Still another example of the trade-offs associated with the operational parameters, and system performance goals of an RF communication system is that associated with data transmission rate versus signal range. As noted above, increasing data transmission rate typically requires increasing the bandwidth of the transmitted signals. Conversely, decreasing data transmission rate typically allows for a reduction in the signal bandwidth. If bandwidth can be reduced, the range of operation will be increased for a given level of power consumption. The foregoing and other trade-offs associated with various operational parameters of a communication system arise in most applications involving RF transmission and reception. The nature of the interrelation between the various operational parameters may vary depending, for example, upon the type of modulation used (such as PPM, FSK, FM, AM), as well as upon the type of coding used.

In the context of IMD systems, there are additional considerations that must be addressed. Primary among these are reliability of transmission and reception, and conservation of the power of the IMD. Conservation of implanted device power, which, in most cases, implies minimizing current drain upon an implanted device's internal battery in particular, renders the aforementioned trade-offs highly significant.

SUMMARY OF THE INVENTION

In one aspect, the present invention implements a method and apparatus for establishing a communications link between an IMD, a patient-worn transponder and a remote monitoring station while, at the same time, minimizing device current drain. Minimal current drain is achieved by scheduling periodic interrogation of the data collected by the IMDs and subsequent retransmission to a remote location. In addition, the IMD may also transmit unscheduled data when a significant event, such as a cardiac arrhythmia or device intervention, occurs.

A further aspect of the present invention provides a communications system that transmits data telemetered from the IMD to a patient-worn device. These data can then be transferred from the patient-worn device, equipped with a Bluetooth (BT) or Home RF (HRF) communication system, to a plurality of nodes similarly equipped with BT or HRF technology. Such wireless data transfer will culminate in the receipt of such data by a transceiver that sends the data to a remote information network and/or medical clinic.

In yet another aspect of the present invention, a telemetry transceiver within the IMD is implemented to communicate data to and from the IMD in an encrypted code. The IMD telemetry transceiver has a range extending outside the patient's body sufficient to reach a patient-worn external device. This external device may be worn on the patient's wrist in one embodiment, or as a neck worn pendant, a modified belt device, or pager-like device attached to the belt in other embodiments. The patient-worn device would have a BT or HRF chip and would re-transmit to a transceiver also equipped with BT or HRF technology, which is connected to a phone line, cellular phone, satellite communication methods, telemetry, or some other means to transmit the data. Accordingly, the patient may move freely around the home and/or yard and still be in communication with the remote network or medical clinic via this method.

DETAILED DESCRIPTION OF THE DRAWINGS

Figure 1:
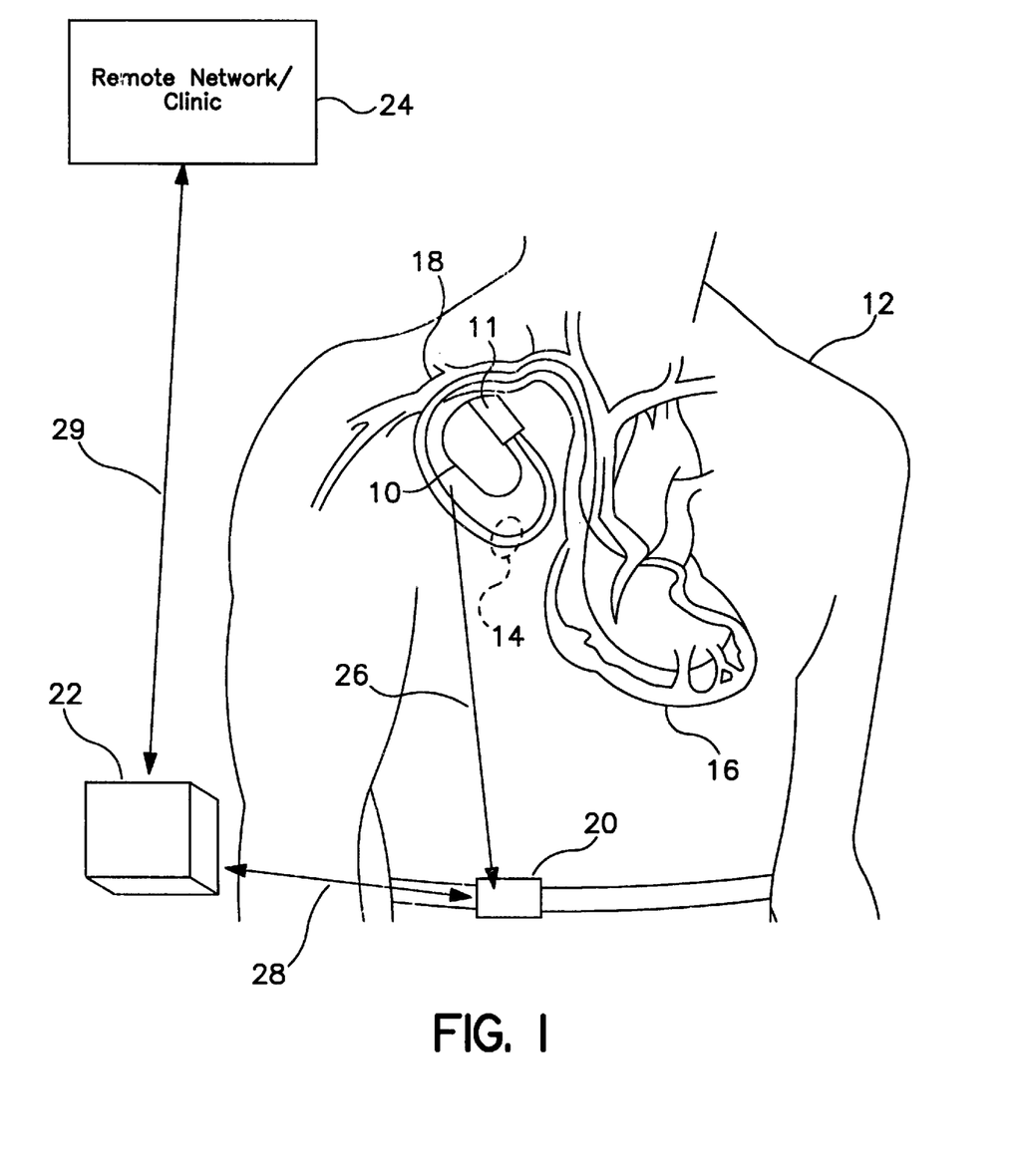
FIG. 1 is an illustration of a body-implantable device system in accordance with the present invention, including a hermetically sealed device implanted in a patient, a patient-worn transponder, an external transceiver, and a remote network/clinic.

FIG. 1 is an illustration of an implantable medical device system adapted for use in accordance with the present invention. The medical device system shown in FIG. 1 includes an implantable device 10—a pacemaker for illustration purposes—that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16.

The present invention will be described herein in an embodiment that includes a pacemaker. Those of ordinary skill in the art, however, with the benefit of the present disclosure will appreciate that the present invention may be advantageously practiced in connection with numerous other types of IMDs such as defibrillators, cardioverters, neurostimulators, and the like. Indeed, the present invention may be practiced in any application in which it is desirable to provide a communication link between two physically separated components.

Also depicted in FIG. 1 is an external patient-worn device 20 for non-invasive, wireless communication with implanted device 10 via uplink and downlink communication channels 26 and 28, to be hereinafter described in further detail. Associated with patient-worn device 20 is a transceiver 22, for facilitating wireless, cellular, or landline communications 29 between transceiver 22 and remote network or medical clinic 24. Patient worn device 20 may alternatively be a wrist-worn or a neck-worn pendant transceiver/control device.

Figure 2:
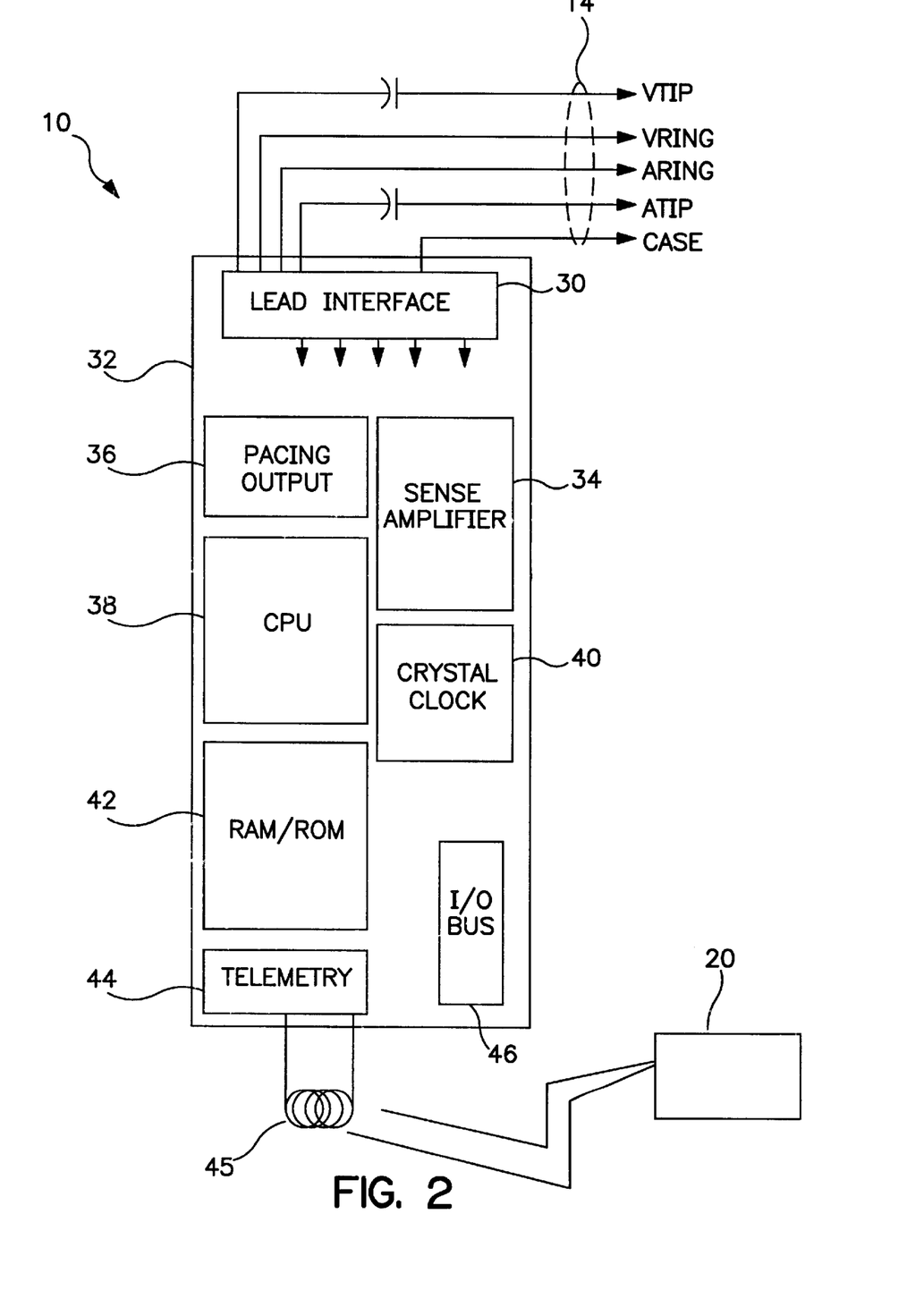
FIG. 2 is a block diagram of the implanted device from FIG. 1.

FIG. 2 is a simplified block diagram of the electronic circuitry that makes up pulse generator 10 in accordance with the presently disclosed invention. As can be seen from FIG. 2, pacemaker 10 comprises a primary stimulation control circuit 32 for controlling the device's pacing and sensing functions. The circuitry associated with stimulation control circuit 32 may be of conventional design, in accordance, for example, with what is disclosed U.S. Pat. No. 5,052,388 issued to Sivula et al., "Method And Apparatus For Implementing Activity Sensing In A Pulse Generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 32 in FIG. 2 includes sense amplifier circuitry 34, stimulating pulse output circuitry 36, a crystal clock 40, a random-access memory and read-only memory (RAM/ROM) unit 42, an I/O Bus 46, and a central processing unit (CPU) 38, all of which are well-known in the art.

Pacemaker 10 also includes internal communication circuit 44 so that it is capable of communicating with external patient-worn device 20 or programmer (not shown) via antenna 45.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 30 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will necessarily be coupled, either directly or indirectly, to sense amplifier circuitry 34 and stimulating pulse output circuit 36, in accordance with common practice, such that cardiac electrical signals may be conveyed to sensing circuitry 34, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 32 includes central processing unit 38 which may be an off-the-shelf programmable microprocessor or micro controller, but in the present invention is a custom integrated circuit.

Although specific connections between CPU 38 and other components of stimulation control circuit 36 are not shown in FIG. 2, it will be apparent to those of ordinary skill in the art that CPU 38 functions to control the timed operation of stimulating pulse output circuit 36 and sense amplifier circuit 34 under control of programming stored in RAM/ROM unit 42. It is believed that those of ordinary skill in the art will be familiar with such an operative arrangement.

With continued reference to FIG. 2, crystal oscillator circuit 40, in the presently preferred embodiment a 32,768-Hz crystal controlled oscillator provides main timing clock signals to stimulation control circuit 32. Again, the lines over which such clocking signals are provided to the various timed components of pulse generator 10 (e.g., microprocessor 38) are omitted from FIG. 2 for the sake of clarity.

It is to be understood that the various components of pulse generator 10 depicted in FIG. 2 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 36, which functions to generate cardiac stimuli under control of signals issued by CPU 38, may be, for example, of the type disclosed in U.S. Pat. No. 4,476,868 to Thompson, entitled "Body Stimulator Output Circuit", which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 34, which is of conventional design, functions to receive electrical cardiac signals from leads 14 and to process such signals to derive event signals reflecting the occurrence of specific cardiac electrical events, including atrial contractions (P-waves) and ventricular contractions (R-waves). Sense amplifier circuit 34 provides these event-indicating signals to CPU 38 for use in controlling the synchronous stimulating operations of pulse generator 10 in accordance with common practice in the art. In addition, these event-indicating signals may be stored as diagnostic data in RAM/ROM 42 and subsequently communicated, via uplink transmission, to external patient-worn device 20 for transmission to transceiver 22 shown in FIG. 1. Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 44 in pacemaker 10, and an associated communication subsystem between external patient-worn device 20 and transceiver 22.

Figure 3:
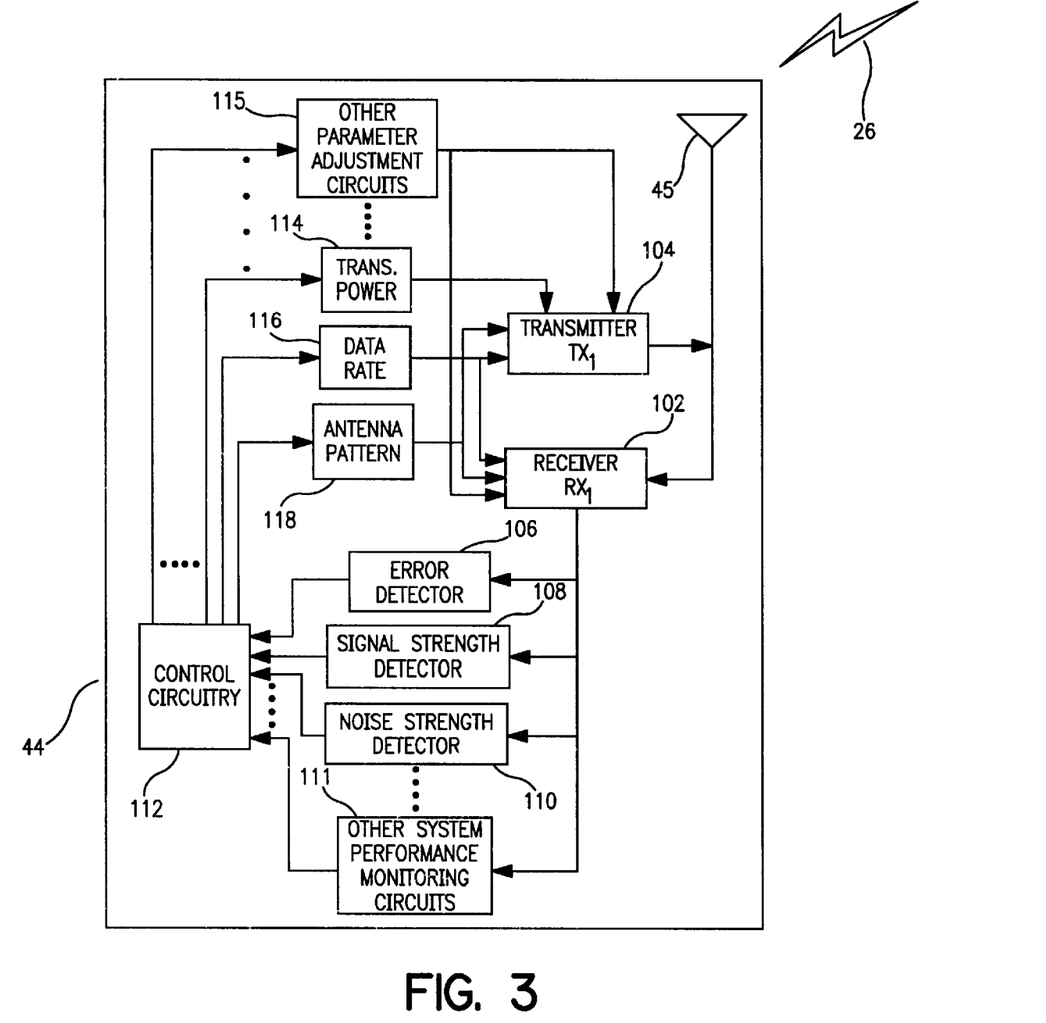
FIG. 3 is a block diagram showing the communication system in accordance with the present invention from the implanted device of FIG. 2.

Referring to FIG. 3, there is shown a simplified block diagram of communication subsystem 44 from pacemaker 10, in accordance with the present invention. Communications subsystem may be, for example, of the type disclosed in U.S. Pat. No. 5,843,139 "Adaptive Performance-Optimizing Communication System for Communicating With an Implanted Medical Device" to Goedeke, et al., which patent is incorporated by reference herein in its entirety.

As described in the '139 patent, communication subsystem 44 in implantable device 10 includes a receiver 102 and a transmitter 104 each coupled to antenna 45 which may be implemented as a multiple-turn wire coil, a stub wire, or a pacing lead. Communication subsystem 44 further includes, in one embodiment, error detection circuitry 106, signal strength detection circuitry 108, and noise strength detection circuitry 110. Generally speaking, error detection circuit 106, signal strength detection circuit 108, and noise strength detection circuit 110, can be called system performance monitoring circuits which function, as that name suggests, to dynamically monitor one or more aspects of communication system 44. Error detection circuit 106, for example, may utilize well-known error detection techniques to determine the bit error rate (BER) and the SNR of digital information received by receiver 102. Signal strength detector circuit 108 may effectively consist of a logarithmic amplifier that detects and filters the RF signal (or IF signal if downconverted) to provide an RSSI (received signal strength indicator) output that gives a voltage proportional to the logarithm of the signal strength at the receiver's RF input. Detector 108 will only respond to the signal present within the receiver pass band. In this way, the desired signal strength (actually, signal plus noise) can be measured. Likewise, the noise can be measured with the same apparatus under the condition of a known period with no received transmission. In this way the signal-to-noise ratio of the received signal can be measured by a simple comparison of the signal and the noise RSSI samples. This method, as would be appreciated by those of ordinary skill in the art, would effectively implement circuit 110 as well as 108 in FIG. 3.

Figure 4:
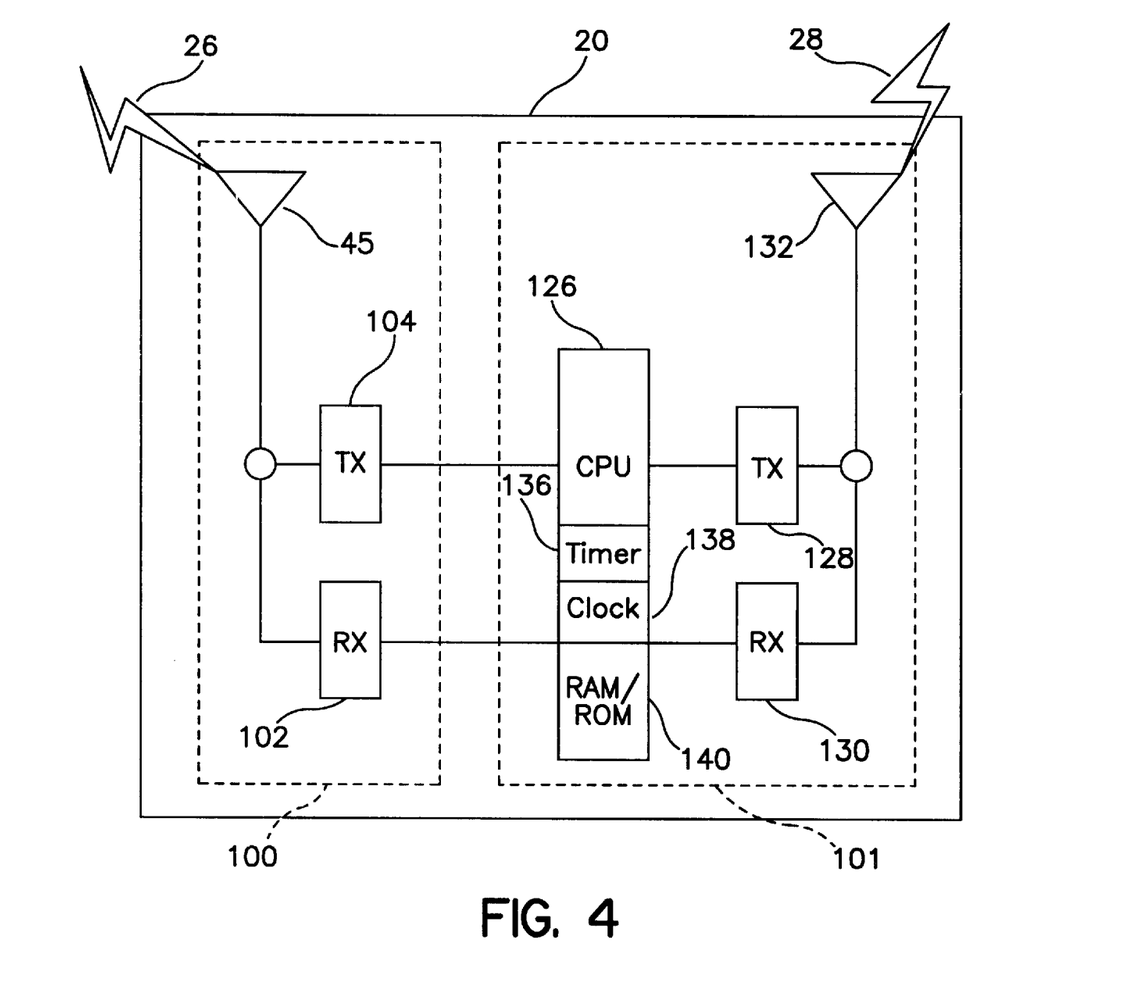
FIG. 4 is a block diagram showing the communication system from the external patient-worn transponder of FIG. 1.

With continued reference to FIG. 3, circuits 106, 108 and 110 are in turn coupled to a control circuit 112 that, in one embodiment, may be a custom integrated circuit or the like. Control circuit 112 in communication subsystem 44 functions to control various aspects of communication operation in device 10, and further functions to cause data to be transmitted to communication subsystem 101 (FIG. 4). For example, as shown in FIG. 3, control circuit 112 is coupled to a transmitter power control circuit 114, such that under command of control circuit 112, the power of signals transmitted by transmitter 104 can be adjusted up or down. Similarly, control circuit 112 is coupled to a data rate control circuit 116 that controls the rate at which data is transmitted from transmitter 104. Control circuit 112 is also coupled to an antenna pattern (field strength as a function of position) control circuit 118, so that the antenna pattern for reception and transmission of transmitted signals may be dynamically configured during operation of communication subsystem 44 and to receiver circuit 102 so that the bandwidth of the bandpass filter therein may be adjusted.

Control circuit 112 is responsive to prioritized sets of operational goals to be accomplished in conjunction with each of a plurality of telemetry transmission types, stored in RAM/ROM 42 (FIG. 2). In response to an identification of the type of telemetry to follow, processor 38 instructs control circuit 112 as to operational parameters and through control circuitry 112 monitors the outputs of the performance monitoring circuits 106, 108, 110, 111. Under control of processor 38, control circuitry adjusts the various parameter adjustment circuits to achieve the operational goals stored in RAM/ROM 42, in order of their priorities. Control circuitry 112 in some cases adjusts the operational parameters associated with transmitter 104 or receiver 102. Alternatively, parameter adjustment commands may be formatted by processor 38 for transmission by transmitter 104 to receiver 102 (FIG. 4), to control corresponding parameter adjustment circuits associated with transmitter 104 (FIG. 4).

In accordance with one of the significant aspects of the invention, communication subsystems 44 and external patient-worn device 20 (FIG. 1) are preferably capable of exchanging information with each other, such that IMD 10 can transmit its telemetry operational parameter data along with the stored patient diagnostic and real-time IMD operational data to external patient-worn device 20. For example, if signal strength detector circuit 108 in subsystem 44 determines that the received signal transmitted from transmitter 120 is unacceptably weak, control circuitry 112 can initiate transmission of a command to subsystem 101 instructing transmitter 120 to increase its transmission power.

The present invention also has applicability of transmitting data either at a pre-determined time, for example, on an hourly basis, upon detection of an arrhythmia, device intervention, and/or status. In accord with the present invention, processor 38 (FIG. 2) receives input from clock 40 to transmit data stored in RAM/ROM 42 at a pre-scheduled, programmed time to external patient-worn device 20. Alternatively, an arrhythmia detected by sense amplifier 34, a therapeutic intervention delivered by pacing output 36, and/or IMD 10 RAM/ROM 42 being filled with diagnostic data will trigger a transmission of the respective data. Other additional types of monitoring may be appropriate depending upon the specific nature of the communication system.

In accordance with one aspect of the present invention, the performance goals of the communication system, and the standards or limits imposed upon operational parameters, may themselves be adjusted on a dynamic basis. The standards for maximum levels of power consumption may also be preferably adjusted on a dynamic, ongoing basis. For example, near the device's end-of-life, power consumption is of critical concern, and it may then be desirable to impose a reduced upper limit on the amount of power consumed by the communication system.

FIG. 4 is a simplified block diagram of an external patient-worn device 20. Communication subsystem 101 is preferably compatible with communication subsystem 44 in implanted device 10 and communicates via RF signals shown diagrammatically as 26. For simplicity in FIG. 4, however, the same numbers used in FIG. 3 for transmitter 104, receiver 102 and antenna 45 are used in communication subsystem 100. Communication subsystem 101 communicates to transceiver 22 via RF signals diagrammatically represented as 29 and is preferably a chip (e.g., integrated circuit) that, in one embodiment, uses Bluetooth (BT) technology. Transmitter 128, receiver 130, and antenna 132 communicate with transceiver 22.

BT technology relies on frequency-hopping, spread spectrum (FHSS) techniques within the 2.4 GHz industrial-scientific-medical (ISM) band (see "Designing Bluetooth Connectivity into Portables", Portable Design, September, 1999, pg 61–63; incorporated herein by reference in its entirety). BT RF chips switch frequencies at 1.6 k hops/s, using a total of 79 1 MHz-wide channels and thus have excellent interference and fading rejection characteristics. The nominal maximum operating distance is 10 meters although the range can be increased to 100 meters with increased transmitter power. Data is transmitted at a maximum rate of up to 1 Mbps. Communication protocol overhead limits the practical data rate to approximately 700 kbps.

One embodiment of a BT network in which the present invention may be practiced consists of only two nodes, patient-worn device 20 and transceiver 22. In this embodiment, the patient is almost always within 30 feet of transceiver 22, for example, within a small home or an apartment. In such cases, there is little or no need for a more extensive network. When the IMD 10 is scheduled to transfer data, it wakes patient-worn device 20 from its standby state. Patient-worn device 20 may page, wake, or transfer data to transceiver 22, or alternatively, store the data for later transmission to transceiver 22. Upon connection and transmission of data to a remote network/clinic 24 (FIG. 1), transceiver 22 directs patient-worn device 20 to again resume the standby mode.

As stated above, BT has a reception/transmission range of approximately 30 feet. In a second embodiment, Home RF (HRF) may be used as the technology to drive communications subsystem 101. HRF has a reception/transmission range of approximately 150 feet. A third embodiment may make use of IEEE 802.11 and its variants.

With continued reference to FIG. 4, microprocessor 126 controls the function of communication subsystems 100 and 101 in transponder 20 via programmable timer 136, clock 138, and programs stored in RAM/ROM 140. A battery (not shown) powers transponder 27. To conserve battery life, the power to the communication subsystem 101 (BT or HRF) is only turned on for the transmission of data to transceiver 22 under the control of microprocessor 126. A preprogrammed timeout (for example, once per hour or day) from timer 136 in patient-worn device 20 allows periodic wakeup of the BT communication subsystem 101 and allows transmission of diagnostic and status data to transceiver 22 via link 28. Alternatively, IMD 10 may initiate a data transmission to patient-worn device 20 and subsequently to transceiver 22 upon a significant event such as an arrhythmia detected, a therapy delivered, diagnostic memory filled, and/or device alarms such as battery ERI, lead defect detected, etc.

FIG. 4 may also illustrate a HRF network 101 in which the present invention may be practiced. Those familiar with HRF technology will be able to appreciate how communication subsystem 101 is able to connect with a wide variety of electronic devices equipped with HRF chips. The HRF specification describes the lowest two layers of a seven-layer OSI network stack model. The two layers are the physical (PHY) and data link control (DLC) layers. The PHY layer sets the data access and range characteristics for the transfer of data, whereas the DLC layer defines the types of data services, such as voice, prioritized streaming, among others. HRF operates in the globally available 2.4 GHz band using frequency hopping spread spectrum at 50–100 hops/s. First generation devices have peak data rates of 1.6 Mb/s and can cover areas within a 150-foot range. Second generation devices use 10 Mb/s peak data rates, with third generation devices having peak data rates of ~20 Mb/s when they become available. HRF devices may include the transmission of voice, video, or computer data, among others.

In the context of FIG. 4, patient-worn device 20 will transfer data to transceiver 22 which may be in contact with remote network or medical clinic 24 (FIG. 1) either trans-telephonically via link 29 or, alternatively, via wireless telemetry (e.g., cellular or satellite communications systems).

Figure 5:
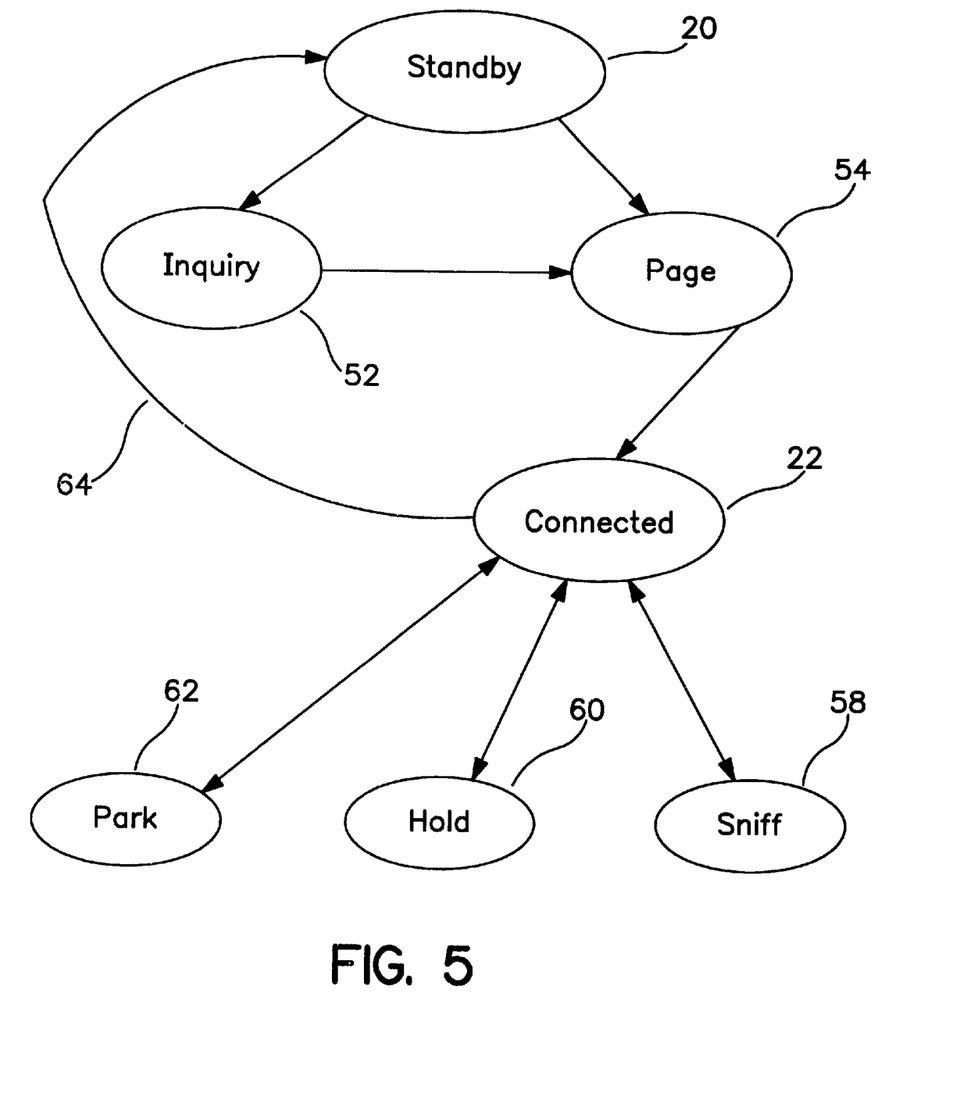
FIG. 5 is an illustration of a BT network in which the present invention may be practiced.

FIG. 5 illustrates a BT or HRF network in which the present invention may be practiced. Those familiar with BT art designate the network illustrated in FIG. 5 as a "piconet" that, in turn and when connected to other piconets, constitutes a BT network. In the interest of consistency with IMD art, the term "network" will hereinafter be used.

Another embodiment, however, does make use of a larger network of nodes. This larger network may be of use in a larger home, a nursing home, or in situations where the patient is mobile and apt to perform yard work, among others. All nodes in such a network (22, and 52 through 66), and including patient-worn device 20 (FIG. 1) remain in a standby mode until IMD 10 is scheduled to transmit its scheduled data transfer—or an arrhythmia or intervention event occurs. When a node "wakes," it becomes the "master." Thus, upon receipt of a transmission from IMD 10, patient-worn device 20 initiates the process of identifying and connecting to a transceiver that, in this case, is node 22. Normally, this would be a direct connection. In certain instances, however, it may become necessary to contact intermediate node 52 and/or 54 before connecting to node 22. In such a case, master node 20 performs inquiries within its range to determine the address of desired node (transceiver) 22. This may take the form of a direct page through node 54, or an inquiry through intermediate node 52 because the address is not known at node 52. Upon connection to desired node (transceiver) 22, master node (patient-worn device) 20 places all other slave nodes (58, 60, and 62) in a sniff, hold, or park mode—to conserve power. Upon connection and transmission of data to a remote network (not shown), node (transceiver) 22 directs master node (patient-worn device) 20 to again resume the standby mode while it is totally powered down by microprocessor 126. Advantageously, such a system uses little current to transmit the information transmitted from the IMD.

Figure 6:
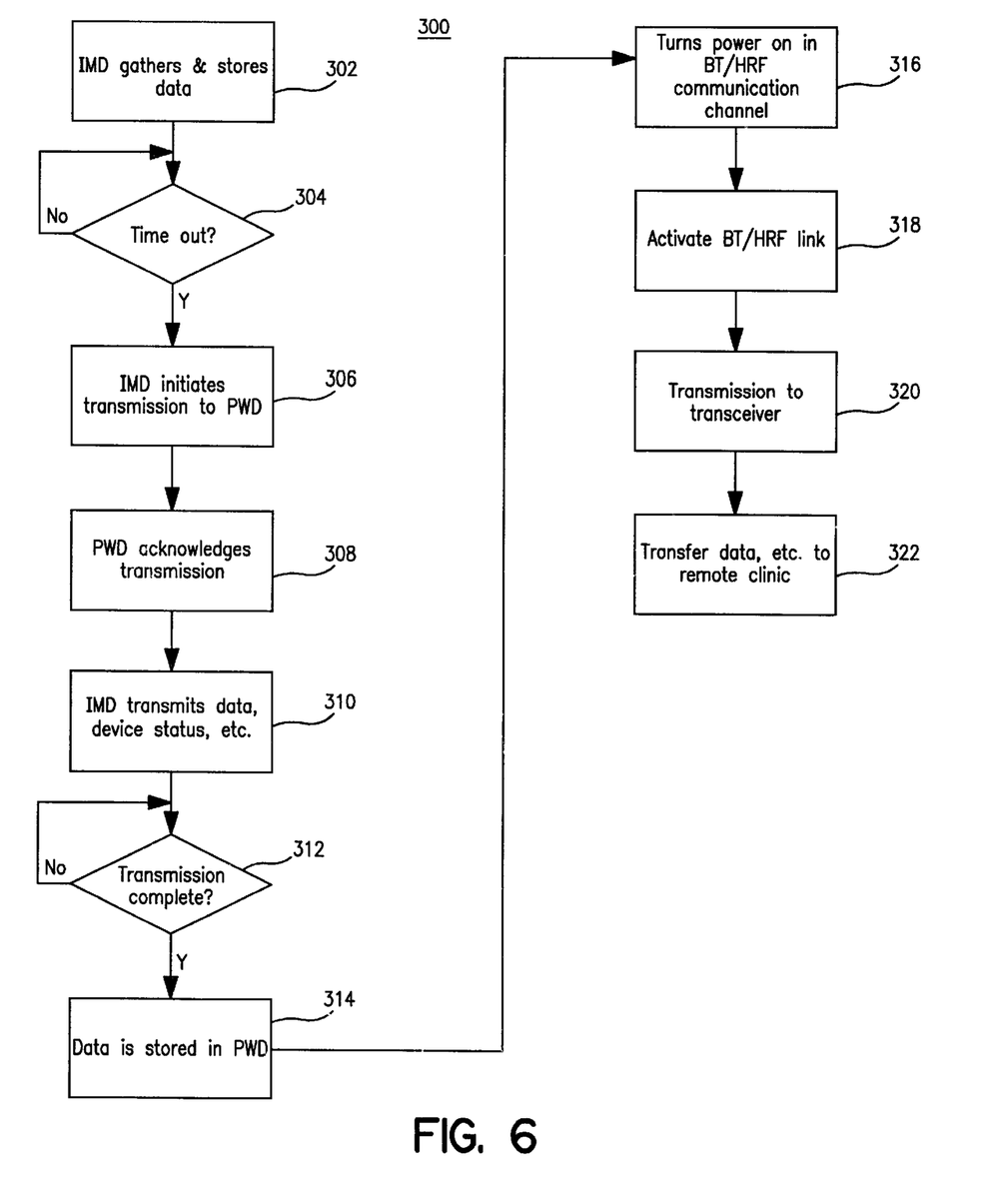
FIG. 6 is a flow diagram of the steps practiced in the present invention.

FIG. 6 is a flow diagram 300 of the transmission of data from IMD 10 to patient-worn device 20, to transceiver 22 and subsequently to remote follow-up clinic or monitoring site 24. Beginning at step 302, IMD 10 gathers diagnostic data and stores it in RAM memory. A timer is activated and the time is compared to pre-programmed duration countdown at step 304. If the time has not been reached the scheduled countdown, timer continues to count. If, on the other hand, the timer reaches its programmed value, a telemetry transmission to the external patient-worn device (PWD) 20 is initiated at step 306. At step 308, the patient-worn device acknowledges the reception to the uplink telemetry from IMD 10. The IMD 10 transmits diagnostic data, device status, patient ID, and error status/log information to the patient-worn device 20. When the transmission is completed at step 312, the data is stored in patient-worn device memory for subsequent retransmission to transceiver 22. Microprocessor 126 turns the power on to the BT or HRF chip at step 316 and the communication channel 101 activates the BT, or alternatively, HRF link at step 318. The data stored in step 314 is transmitted to transceiver 22 at step 320. Upon completion, the data is then transmitted to a remote network/clinic at step 322 via telephone landlines, cellular, satellite or other wireless links.

Those with ordinary skill in the art will appreciate how this technology may be further applied to ensure that data from an IMD may be uplinked to a BT- or HRF-equipped transceiver and, from there, to remote network or medical clinic 24.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A communications system for implantable medical device (IMD) data management, comprising:
   a remote monitoring station;
   a patient-worn transponder that wakes from a standby state in response to a telemetry transmission from an implanted medical device;
   a communications link between the remote monitoring station and the patient-worn transponder; and
   an implantable medical device (IMD) including a data communications subsystem and a control circuit that gathers diagnostic data and stores it until a timer reaches a scheduled countdown whereupon the data communications subsystem is activated to produce a telemetry transmission to the patient-worn transponder.

2. The system of claim 1, wherein the patient-worn transponder includes a communication channel implemented in Bluetooth technology.

3. The system of claim 1 wherein the patient-worn transponder includes a communication channel implemented in Home RE (HRF) technology.

4. The system of claim 1 wherein the patient-worn transponder includes a memory store data transmitted from the IMD for subsequent transmission to the remote monitoring station.

* * * * *

UNITED STATES PATENT AND TRADEMARK OFFICE
CERTIFICATE OF CORRECTION

PATENT NO. : 6,577,901 B2
DATED : June 10, 2003
INVENTOR(S) : David L. Thompson It is certified that error appears in the above-identified patent and that said Letters Patent is hereby corrected as shown below:

Column 12,
Line 8, delete "Home RE" and insert -- Home RF --.
Line 10, delete "memory store" and insert -- memory to store --.

Signed and Sealed this

Eighth Day of February, 2005

JON W. DUDAS
*Director of the United States Patent and Trademark Office*